United States Patent
Brehm et al.

(10) Patent No.: US 10,071,582 B2
(45) Date of Patent: Sep. 11, 2018

(54) APPARATUS AND METHODS FOR LABELING VIALS OR AMPOULES STORED AT TEMPERATURES AS LOW AS −200° C

(71) Applicant: MERIAL INC., Duluth, GA (US)

(72) Inventors: Andy Brehm, Jefferson, GA (US); Julie Campbell, Baldwin, GA (US); Ed Schindler, Snellville, GA (US); Dennis Jerome Freeman, Cleveland, GA (US)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 15/498,933

(22) PCT Filed: Oct. 30, 2015

(86) PCT No.: PCT/US2015/058209
§ 371 (c)(1),
(2) Date: Apr. 27, 2017

(87) PCT Pub. No.: WO2016/069984
PCT Pub. Date: May 6, 2016

(65) Prior Publication Data
US 2017/0246897 A1    Aug. 31, 2017

Related U.S. Application Data

(60) Provisional application No. 62/072,695, filed on Oct. 30, 2014.

(51) Int. Cl.
*B41M 5/24* (2006.01)
*B41J 3/407* (2006.01)
*A61J 1/18* (2006.01)

(52) U.S. Cl.
CPC .......... *B41M 5/24* (2013.01); *A61J 1/18* (2013.01); *B41J 3/4075* (2013.01); *A61J 2200/44* (2013.01)

(58) Field of Classification Search
CPC ...... B41M 5/24; B41M 2205/04; B41J 3/407; B41J 3/4075; A61J 1/1468; A61J 1/05
See application file for complete search history.

(56) References Cited

U.S. PATENT DOCUMENTS

| | | |
|---|---|---|
| 6,818,859 B2 | 11/2004 | Lodge |
| 7,647,867 B2 | 1/2010 | Byron |
| 9,358,091 B2 * | 6/2016 | Gilligan ............... A61D 19/024 |
| 2011/0126979 A1 | 6/2011 | Ambartsoumian |
| 2012/0089490 A1 | 4/2012 | Blaine |
| 2017/0312852 A1 * | 11/2017 | Brehm ................ B23K 26/127 |

FOREIGN PATENT DOCUMENTS

WO    WO 2014/063052 A1    4/2014

OTHER PUBLICATIONS

U.S. Appl. No. 15/499,127, Not yet published, Merial, Inc.

* cited by examiner

*Primary Examiner* — Huan Tran
(74) *Attorney, Agent, or Firm* — Judy Jarecki-Black; Patrick Lowder; Merial Inc.

(57) ABSTRACT

This invention relates to an apparatus and method for applying writings and other markings to a frozen vial or ampoule, which is filled with biological material, and which is held at temperatures between about −70° C. and about −196° C. More particularly, the invention relates to a laser marking method that allows frozen vials to be labeled, while maintaining the integrity of the biological material contained therein.

30 Claims, 4 Drawing Sheets

APPARATUS AND METHODS FOR LABELING VIALS OR AMPOULES STORED AT TEMPERATURES AS LOW AS -200° C

CROSS-REFERENCE TO OTHER APPLICATIONS

This application claims priority to U.S. provisional patent application 62/072,695, which was filed on Oct. 30, 2014, and is herein incorporated by reference in its entirety.

INCORPORATION BY REFERENCE

All references cited herein are incorporated by reference herein in their entirety.

FIELD OF THE INVENTION

This invention relates to an apparatus and method for imprinting a vial or ampoule, which is held at temperatures at around that of liquid nitrogen. More particularly, but not by way of limitation, this invention relates to a laser printing system and method for printing onto a vial or ampoule that is at a temperature as low as the gaseous phase above liquid $N_2$ or the liquid phase of liquid $N_2$, at standard atmospheric pressure.

BACKGROUND OF THE INVENTION

In situations where vials or ampoules contain veterinary and pharmaceutical medications (e.g. immunological compositions, including vaccines), certain information such as the type of medicine, dosage amount, manufacturer, expiration date, etc. must be clearly imprinted on each vial to remain in compliance with the regulations of the various regulatory agencies. Additionally, the number of vials or ampoules filled and the lot from which material originated are also very important data points to mark and track. Prior art labeling techniques include printing onto a label, and then placing the label onto the vials. More recent efforts include printing directly onto the vials (see U.S. Pat. No. 7,647,867, to Byron). In another example, US 20140048066 A1 (to Holitas Limited) describes the labeling of nebulizer ampoules by laser-marking or laser-engraving data on a film to produce a data film and affixing the film onto a nebulizer ampoule using a non-migratory adhesive. To date, applicants are aware of no method that allows frozen vials or ampoules to be labeled, while still preserving the integrity and efficacy of the biological material contained therein.

For multi-national pharmaceutical companies, where the same product requires different labeling (i.e. owing to different languages and different regulatory requirements), the ability to label a filled, frozen vial would be highly desirable. The benefits to the supply chain are obvious (e.g. faster lead time, less waste, increased flexibility, etc.) Unfortunately, raising the temperature of a frozen vial to the temperatures normally associated with label application and/or printing is well-known to unacceptably reduce the biological activity of the vial's contents. Thus, the application of heated labels, as disclosed in US20080178988A1 (to Ambarsoumian), would subject the sensitive biological material to unacceptable heating. Moreover, any efforts in using a laser or other means to directly mark the glass of the vial or ampoule would almost certainly subject the frozen biological material to unacceptable heat stress.

Accordingly, there remains a long-felt need to develop a method to label vials containing frozen medicaments, including vaccines, while retaining the required biological activity, including immunological activity. This disclosure provides a solution to this long-felt need.

SUMMARY OF THE INVENTION

Embodiments of the invention provide methods of forming writings and graphics on a label, or other suitable substrate, held at cryogenic freezing temperatures, for example, at least as low as the gaseous phase above liquid nitrogen (i.e. about −196° C., or the boiling point of liquid nitrogen at standard atmospheric pressure). In accordance with one aspect of the invention, a method of forming a graphic on a label or substrate comprises applying a laser beam to a laser-active coating on a surface of an article to mark a writing or graphic in the laser-active coating.

The laser-active coating may comprise a polymer binder and a pigment, and optionally may contain additional ingredients. The coating formulation may contain at least a polymer binder having a glass transition temperature which provides a desired effect upon activation of the formulation by a laser beam, and a pigment having a heat resistance and present in a concentration which provide a desired effect upon activation of the formulation by the laser beam.

Suitable materials for "blank labels," which are ready to be ablated by the action of a laser beam, to reveal the desired writings or graphics, include, but are not limited to: plastics, acrylics, vinyls, polyethylene terephthalate (e.g., MYLAR®), polycarbonates (e.g. LEXAN®), or the like.

In a broad sense, this disclosure provides a method for applying writings, graphics and/or markings to cryogenically frozen vials or ampoules, while maintaining the integrity, including potency or efficacy, of the biological contents contained therein, comprising the following steps (see also FIG. 6, which presents a flow diagram for this process):

1. applying a blank, laser-active label to a storage vial or ampoule;
2. depyrogenating/sterilizing the blank labeled vial or ampoule;
3. filling the vial or ampoule with product/material to be cryogenically stored/frozen;
4. placing the filled vials or ampoules into storage apparatus (e.g. ampoules placed into aluminum canes);
5. freezing the vials or ampoules to temperatures as low as about that of liquid nitrogen at standard atmospheric pressure (or about −196° C.);
6. transferring the frozen vials or ampoules to long-term and/or permanent storage at a temperature as low as about −196° C.;
7. testing the frozen material for integrity, including potency or efficacy;
8. determining the dose presentation/product specifications based upon the activity test; wherein after satisfactory testing and release, the containers which meet required specifications will be retrieved from the long-term or permanent controlled storage area and placed into intermediate storage area, while maintaining the low temperature of about −196° C., to ensure the integrity of the biological material;
9. using a laser to apply writings or graphics to the blank labeled ampoules or vials based upon product specifications/information/approved label as defined by the testing, the customer specifications, and regulatory governance.

Other aspects of the invention, including apparatus, systems, methods, and the like which constitute part of the invention, will become more apparent upon reading the following detailed description of the exemplary embodiments and viewing the drawings.

DETAILED DESCRIPTION OF THE INVENTION

Figure 1:
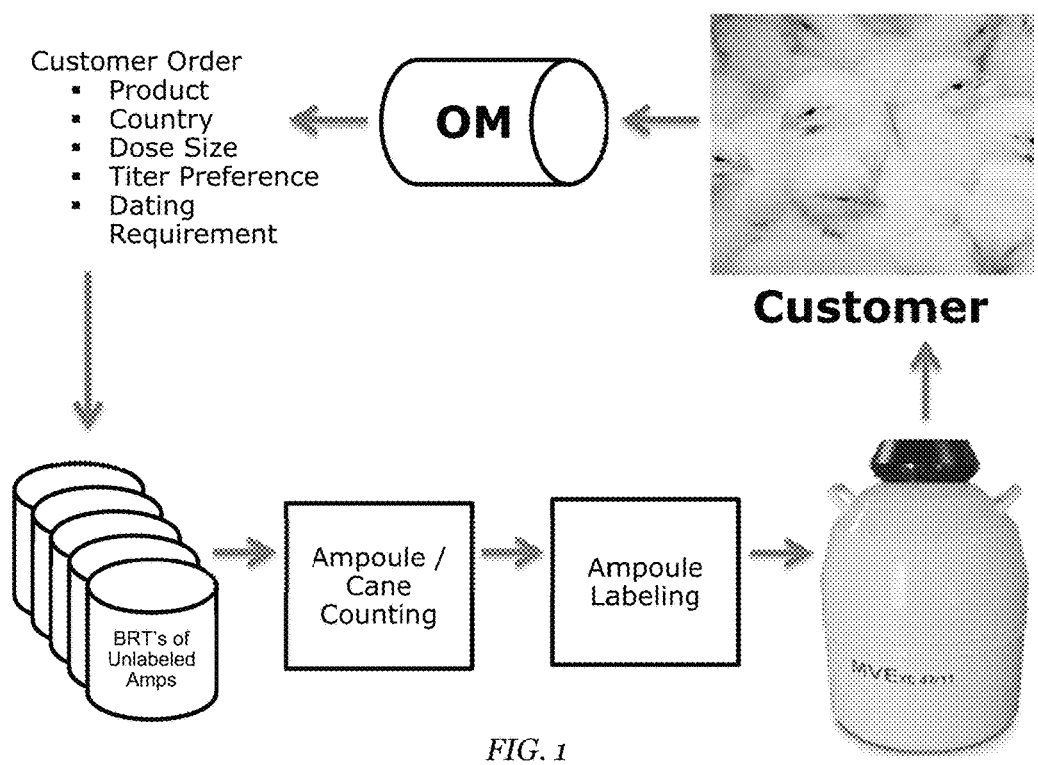
FIG. 1 presents a flow diagram for the inventive labeling process.
Figure 2:
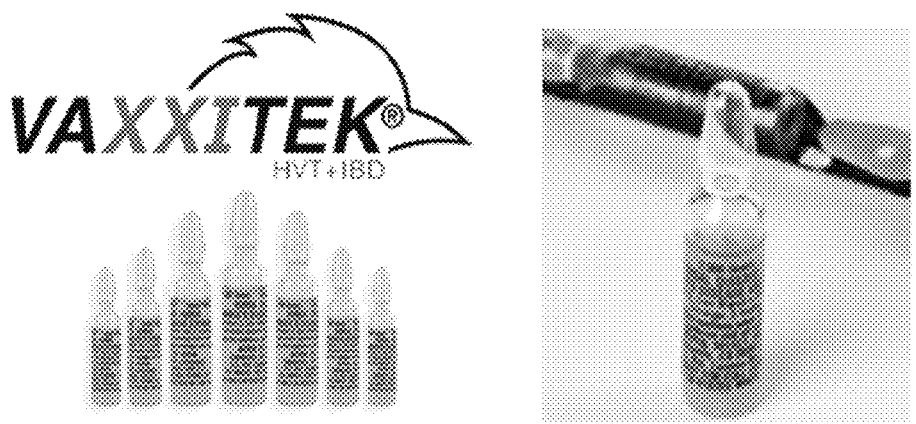
FIG. 2 shows VAXXITEK® ampoules, labeled prior to freezing.
Figure 3:
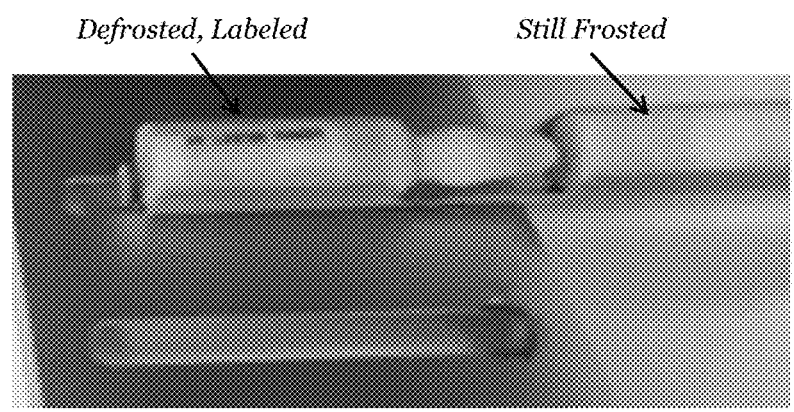
FIG. 3 shows ampoules pre-labeled with laser-active blank labels.

In an aspect of the invention, the disclosure provides for a method for applying writings, graphics and/or markings to blank labels, which are affixed to ampoules or vials, and which are held at temperatures as low as about −196° C. (i.e. at about the temperature of liquid nitrogen at standard atmospheric pressure.

In an embodiment, the method generally includes the steps of applying a blank label to unfilled ampoules, filling the ampoules with a biological material, freezing the ampoules, testing the ampoules, storing the ampoules, taking the ampoules out of storage for labeling, removing laser-blocking vapor, using a first laser to remove the layer of frost from atop the blank label, and using a second laser to apply the writing, graphics and/or markings.

In advantageous embodiments, the entire method is carried out in cool, dry nitrogen gas, to eliminate the need to remove water vapor or frost. In such an embodiment, the disclosure provides a method for applying writings, graphics and/or other markings to frozen vials or ampoules, while maintaining the integrity of the biological material contained therein, comprising the following steps:
   a. providing a plurality of biological material-filled vials, which are held at about −70° C. to about −196° C., and to which blank laser-ablatable labels had previously been applied;
   b. loading the plurality of vials into a temperature-controlled marking enclosure, which is substantially filled with dry nitrogen gas to reduce or eliminate the presence of moisture inside the enclosure;
   c. conveying the vials beneath marking lasers;
   d. applying laser light to the laser-ablatable labels;
   e. determining whether the vials have been marked to within required specifications, thereby applying writings, graphics and/or other markings to frozen vials, while maintaining the integrity of the biological material contained therein.

In one embodiment, the integrity of the biological material may be confirmed as having been maintained if the biological material is capable of eliciting an immune response in a target animal. The elicited response is statistically similar to the response elicited by the biological material contained within the plurality of vials prior to being subjected to the laser-marking method.

In an embodiment, the integrity of the biological material may be confirmed as having been maintained if the biological material is determined by ELISA, virus neutralization antibody (VNA) test, or any other suitable immunological measuring test, to be within the specifications required by the product specifications for the biological material.

In a particular embodiment, the vials are conveyed along conveyor belts. In an advantageous embodiment, two or more rows of vials are conveyed beneath the marking lasers to increase the speed at which the vials may be marked.

In another embodiment, the method may further comprise the step of transferring the marked vials to a liquid nitrogen-containing shipping Dewar. Advantageously, the Dewar comprises a means for reversibly connecting to the marking enclosure, such that the marked vials may be transferred via a means for transferring the vials to the storage/shipping Dewar, without exposing the vials to the air outside of the enclosure.

In another embodiment, the invention provides a method for applying writings, graphics and/or other markings to vials held at a temperature from about −70° C. to about −196° C., while maintaining the integrity of the biological material contained therein, comprising the following steps:
   a. applying blank laser-ablatable labels to a plurality of cryogenic storage vials;
   b. depyrogenating/sterilizing the vials;
   c. filling the vials with biological material;
   d. placing the filled vials into a storage means;
   e. transferring the vials to a means for marking the vials with lasers;
   f. using a laser to apply writings, graphics and/or other markings to the vials, thereby applying writings, graphics and/or other markings to the frozen vials, while maintaining the integrity of the biological material contained within the vials.

In an embodiment, the method may further comprise the steps of:
   a. freezing the vials at a controlled rate of cooling, prior to placing the vials into the storage means;
   b. transferring the frozen vials to long-term and/or permanent storage at a temperature as low as the gaseous or liquid phase of $N_2$ (about −196° C.);
   c. testing the frozen material for activity;
   d. determining the dose presentation/product specifications based upon the activity test; wherein after satisfactory testing and release, the containers which meet required specifications will be retrieved from the long-term or permanent controlled storage area and placed into intermediate storage area to facilitate the steps recited in (j), all of which are conducted in the gaseous phase of $N_2$ to ensure product integrity;
   e. counting the containers to ensure adequate reconciliation for customer requests/orders;

f. using a laser to apply writings, graphics and/or other markings to the ampoules or vials, based upon product specifications/information/approved label as defined by the testing, the customer specifications, and regulatory governance.

In one embodiment, the applying of writings and markings step comprises removing laser light-blocking vapor, if present, by applying a short burst of dry air prior to applying the laser light to the previously affixed blank label.

In advantageous embodiments, the applying of writings and markings step is carried out in a temperature-controlled enclosure containing dry nitrogen gas, which gas is held at temperatures below about −70° C. or below about −80° C.

In an embodiment, the method comprises the step of placing the marked vials into one or more cryogenic shipping vessel.

In some embodiments, the material in the vial is a vaccine, including a cell-associated live vaccine.

In advantageous embodiments, the vaccine loses less than about 0.2 log of titer during the labeling procedure. In an even more advantageous embodiment, the vaccine loses less than about 0.1 log of titer during the labeling procedure.

In an alternative embodiment, the method includes the following steps:
1. applying a blank, laser-active label to a storage vial or ampoule;
2. depyrogenating/sterilizing the blank labeled vial or ampoule;
3. filling the vial or ampoule with product/material to be cryogenically stored/frozen;
4. placing the filled vials or ampoules into storage apparatus (e.g. ampoules placed into aluminum canes);
5. freezing the vials or ampoules to temperatures as low as about that of liquid nitrogen at standard atmospheric pressure (i.e. about −196° C.);
6. transferring the frozen vials or ampoules to long-term and/or permanent storage at a temperature as low as about −196° C.;
7. testing the frozen material for integrity, including potency or efficacy;
8. determining the dose presentation/product specifications based upon the activity test; wherein after satisfactory testing and release, the containers which meet required specifications will be retrieved from the long-term or permanent controlled storage area and placed into intermediate storage area, while maintaining the low temperature of about −196° C., to ensure the integrity of the biological material;
9. using a laser to apply writings, graphics and/or markings to the blank labeled ampoules or vials based upon product specifications/information/approved label as defined by the testing, the customer specifications, and regulatory governance; thereby applying the writings, graphics and/or markings to the cryogenically frozen ampoules or vials.

In yet another embodiment, the entire method may be carried out at less than about −70° C., −80° C., −90° C., −100° C., −110° C., −120° C., −130° C., −140° C., −150° C., −160° C., −170° C., −180° C., −190° C., or less than about 200° C. In general, temperatures of less than about −80° C. may be used in the practice of the disclosed method. However, temperatures above about −60° C. should be avoided, particularly for the labeling of ampoules containing cell-associated live vaccines (e.g. Merial's Marek's vaccine), as higher temperatures may compromise the integrity of the biological materials.

Accordingly, in one embodiment, the application of writings, graphics and/or markings step may be carried out using the following steps, each carried out at less than about −80° C.:
1. positioning the ampoule or vial such that it is within range of a first laser;
2. applying appropriately chilled compressed air to remove the light-obstructing vapor (i.e. the "cloud-like" condensate, which accumulates in the air when temperatures are near to the boiling point of liquid nitrogen);
3. applying a sufficient amount of laser energy from the first laser to the frost layer to remove said frost layer from the surface of the ampoule's blank label;
4. positioning the ampoule or vial such that it is within range of a second laser;
5. applying a sufficient amount of energy to an outer layer of the blank label to ablate away portions of the outer layer; thereby allowing an inner layer of the label to become visible.

Figure 4A:
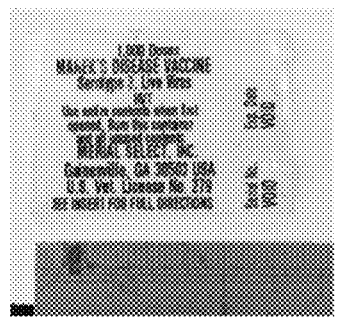
FIG. 4A shows a label produced using the old method of imprinting on the label prior to applying the label to the ampoule.
Figure 4B:
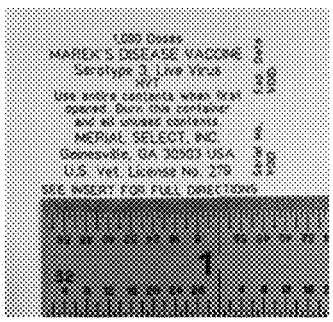
FIG. 4B shows a new label, produced by laser marking (datalasing) of black on white background.
Figure 5A:
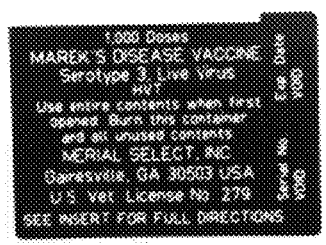
FIG. 5A shows a new label, produced by laser ablation of the outermost black layer, which revealed the white layer.
Figure 5B:
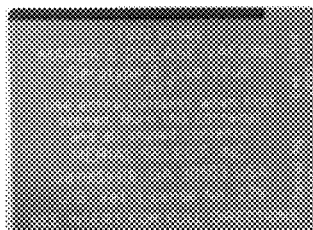
FIG. 5B shows a label, produced by laser ablation of the outermost yellow layer, which revealed the white layer.
Figure 5C:
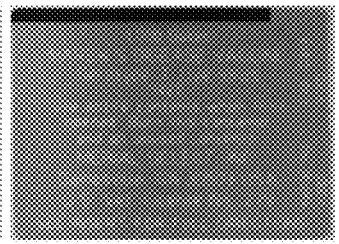
FIG. 5C shows a label, produced by laser ablation of the outermost red layer, which revealed the white layer.

In such an embodiment, the second laser is used to ablate away specific portions of the outer layer of a multi-layered blank label, such that the writings, graphics and/or markings are revealed by a laser ablation technique. FIG. 4A shows a label produced using the existing method (i.e. printing of the label prior to application to the ampoule), and FIG. 4B shows a label produced using the inventive method (i.e. writings were applied to the label on cryogenically frozen ampoules using laser ablation).

Use of such a laser ablation technique allows for additional label layers to be included as needed, for example, to prevent thermal transfer during the frost removal or laser ablation steps. It is essential that the integrity/efficacy/potency of the cryogenically frozen biological material is maintained during the entire process.

In an alternative embodiment, the temperature could be maintained in such a way as to avoid the accumulation of the light-obstructing vapor, thereby obviating the need to use compressed air to remove said vapor. In a particularly useful embodiment, the laser labeling method may be carried out in a substantially or completely contained environment. For example, the method could be performed within an enclosure comprising vacuum-jacketed walls, similar to those used in the construction of cryogenic Dewars.

In a particular embodiment, the method is carried out in an enclosed environment and the temperature is maintained at less than about −80° C. To minimize or eliminate the deposition of frost on the ampoules, the enclosure is continually supplied with dry nitrogen gas. In order to maintain the desired temperature during the practice of the method, the pressure of the enclosure may be monitored and adjusted using any means routine in the art.

The nature of the label material is not particularly limited. The label substrate must be able to adhere to the ampoules or vials at about room temperature and stand up to the subsequent sterilization and cryogenic freezing processes. Representative classes and examples of label materials that may be utilized include, but are not necessarily limited to, plastics, acrylics, vinyls, polyethylene terephthalate (e.g., MYLAR®), polycarbonates (e.g. LEXAN®) or the like.

In an embodiment, the product testing includes potency testing, which may include the determination of titer or plaque forming units (PFU's).

In an embodiment, labels may comprise multiple layers. The multiple layers may comprise a primary (interior) layer which may be, for example, dark or black, or, light or white. If the interior layer is light or white in color, the marking may be dark or black. Conversely, if the interior color is dark or black, the marking color may be light or white.

In an embodiment, the secondary (outer) layer may be colored coded based upon marketing preference. Variable coloring allows for visual differentiation of container contents or material specifications.

Additional layers may be added to allow for further differentiation of material/containers. In an embodiment, the primary or interior layer(s) is a polyester face stock. The secondary/additional layer(s) may be a colored polyester face stock.

In an embodiment, the laser ablation method provides color-coding for different types of biological products. For example, all Marek's Disease vaccines could have an orange label with black lettering. All combinations of background and foreground colors are contemplated, for example, but not limited to white lettering on black background, white lettering on blue background, white lettering on purple background, and so on.

In another embodiment, "datalase" (DataLase Inc.) labels may be used. This technology uses a combination of color change chemistry and low power laser light. In such an embodiment, all of the other steps would be the same (e.g. blowing away the light-blocking cloud and using a laser to remove the frost layer from the surface of the label). The only step that would change is that "datalasing" would be used in place of laser ablation.

In an embodiment, the laser may be selected from one of ID Technology's "Macsa" range of lasers, including, but not limited to, the Kioio plus laser. In another embodiment, an Ultra High Speed (UHS) laser may be used. In yet another embodiment, an extremely powerful Bow laser may be used. Now that applicants have made the instant disclosure, those skilled in the art may employ any number of suitable lasers to practice the invention. $CO_2$ and YAG pumped diode lasers are among the many possible choices.

In a particular embodiment, the laser may have the following characteristics:
  Ability to print two (2) lines of text at 16,000 units per minute;
  A digital circuit board driving a fast mirror tracking system;
  Consistent, high-quality, permanent marking;
  Ability to mark on labels, cardboard, PET, glass, coating and wood;
  Ability to operate with a handheld terminal, touch screen or PC;
  Available in 30 and 60 watt power.

For example, IDT Laser Systems "SHS" Laser Coders utilize digital circuit boards to control its mirrors, freeing the laser to mark at super high speeds. Applying laser energy quickly and efficiently may reduce the amount of heat to which the frozen ampoules must be subjected during the frost removal and laser marking steps.

In some embodiments, multiple lasers may be used. For example, a more powerful laser may remove the frost, and a less powerful laser may ablate the outer label to produce the marking. Alternatively, the same laser may serve both functions of frost removal and label layer ablation.

The invention with be further described by the following Examples.

EXAMPLES

Example 1. Labeling and Simulating the Handling of the Frozen Ampoules to Ensure the Laser Ablation Process does not Unacceptably Affect the Biological Materials Regulatory agencies have strict requirements governing the methods used to produce and qualify biological materials. For example, vaccine manufacturers must have protocols for evaluating the efficacy of the biological samples, and they must provide "retention samples" to the regulatory agencies. As a consequence, some of the ampoules flow into commerce, and some go to the regulatory agencies. It was the object of this example to simulate this differential handling of frozen ampoules, to make sure the disclosed laser ablation labeling process would not only effectively apply writings and marking to cryogenically frozen ampoules, but do so in such a way as to maintain strict compliance with all regulatory standards.

Example 2. Automating the Laser Ablation of Frozen Ampoules

Figure 6:
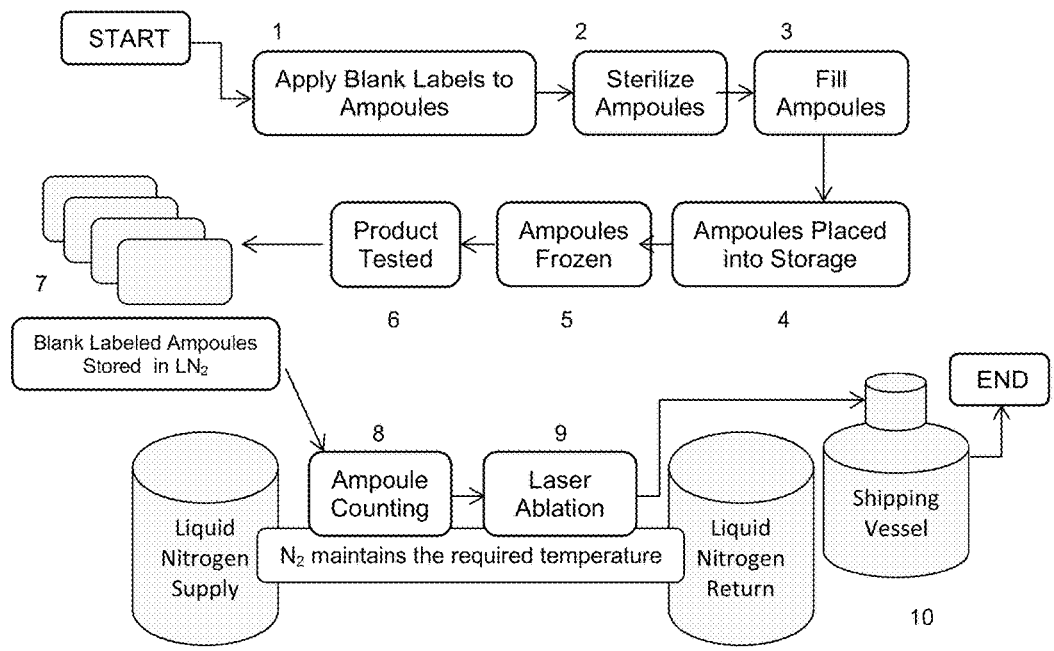
FIG. 6 is a flow diagram of the complete labeling process. Blanks are first applied to the ampoules (1), followed by sterilization (2) and filling (3). Next, ampoules are placed into a storage apparatus (4) and frozen using a suitable cooling protocol (5). At this stage, a portion of the ampoules must be taken out for testing (6), while the balance of the ampoules are stored in liquid nitrogen. Based upon the testing results, business needs, and compliance requirements, the stored ampoules are then counted (8) and labeled (9), all the while being maintained at a sufficiently cold temperature using liquid $N_2$. Finally, the labeled ampoules are placed in appropriate shipping containers (10).

A temperature controlled enclosure was designed to carry out the above-detailed laser labeling method, as generally schematized in FIG. 6. Initially, a plurality of blank labeled ampoules are filled with biological materials and frozen to between about −70° C. to about −196° C. Thereafter, the frozen ampoules are loaded into the enclosure via a loading means (for example, a hopper), which is capable of transferring frozen vials to a laser labeling region of the enclosure. A conveyance means then conveys the ampoules such that they pass beneath lasers, which apply the required markings to the previously applied blank labels. The labeled ampoules are then scanned by a plurality of cameras, and a means for processing images then determines whether the applied markings are within the required specifications. Improperly labeled ampoules may be removed automatically, and processors controlling the lasers may be instructed to modify the laser parameters to correct the defects noted by the image processing means. The marked frozen ampoules are ultimately transferred to Dewars for storage/shipping.

To ensure integrity of the biological materials, the frozen ampoules are maintained at less than about −70° C. throughout the entire laser labeling process, up to and including the final transfer of the ampoules to the storage/shipping Dewar. The entire laser labeling enclosure may be operated inside a walk-in cold room to reduce temperature losses experienced by the enclosure. Alternatively or additionally, the enclosure may comprise airlocks to prevent outside air, which may contain moisture, from entering into the areas of the enclosure where the lasers are used to apply markings to the frozen ampoules. Preventing moisture from entering the dry nitrogen gas-filled enclosure eliminates the formation of vapor or frost, which would otherwise obscure the laser light from making the required markings on the ampoules.

What is claimed:

1. A method for applying writings, graphics and/or other markings to frozen vials or ampoules, while maintaining the integrity of the biological material contained therein, comprising the following steps:
  a. providing a plurality of biological material-filled vials, which are held at about −70° C. to about −196° C., and to which blank laser-ablatable labels had previously been applied;
  b. loading the plurality of vials into a temperature-controlled marking enclosure, which is substantially filled with dry nitrogen gas to reduce or eliminate the presence of moisture inside the enclosure;
  c. conveying the vials beneath marking lasers;
  d. applying laser light to the laser-ablatable labels;
  e. determining whether the vials have been marked to within required specifications, thereby applying writings, graphics and/or other markings to frozen vials, while maintaining the integrity of the biological material contained therein.

2. The method of claim 1, wherein the integrity of the biological material is confirmed as having been maintained if the biological material is capable of eliciting an immune response in a target animal.

3. The method of claim 2, wherein the elicited response is statistically similar to the response elicited by the biological material contained within the plurality of vials prior to being subjected to the laser-marking method.

4. The method of claim 1, wherein the integrity of the biological material is confirmed as having been maintained if the biological material is determined by ELISA, virus neutralization antibody (VNA), or any other suitable immunological measuring test, to be within the specifications required by the product specifications for the biological material.

5. The method of claim 1, wherein the vials are conveyed along conveyor belts.

6. The method of claim 1, wherein two or more rows of vials are conveyed beneath the lasers to increase the speed at which the vials are marked.

7. The method of claim 1, further comprising the step of transferring the marked vials to a liquid nitrogen-containing shipping Dewar.

8. The method of claim 7, wherein the Dewar containing a means for reversibly connecting to the marking enclosure, such that the marked vials may be transferred via a means for transferring the vials to the storage/shipping Dewar, without exposing the vials to the air outside of the enclosure.

9. A method for applying writings, graphics and/or other markings to vials held at a temperature from about −70° C. to about −196° C., while maintaining the integrity of the biological material contained therein, comprising the following steps:

a. applying blank laser-ablatable labels to a plurality of cryogenic storage vials;
b. depyrogenating/sterilizing the vials;
c. filling the vials with biological material;
d. placing the filled vials into a storage means;
e. transferring the vials to a means for marking the vials with lasers;
f. using a laser to apply writings, graphics and/or other markings to the vials, thereby applying writings, graphics and/or other markings to the frozen vials, while maintaining the integrity of the biological material contained within the vials.

10. The method of claim 9, further comprising the steps of:

a. freezing the vials at a controlled rate of cooling, prior to placing the vials into the storage means;
b. transferring the frozen vials to long-term and/or permanent storage at a temperature as low as the gaseous or liquid phase of $N_2$ (about −196° C.);
c. testing the frozen material for activity;
d. determining the dose presentation/product specifications based upon the activity test; wherein after satisfactory testing and release, the containers which meet required specifications will be retrieved from the long-term or permanent controlled storage area and placed into intermediate storage area to facilitate the steps recited in (j), all of which are conducted in the gaseous phase of $N_2$ to ensure product integrity;
e. counting the containers to ensure adequate reconciliation for customer requests/orders;
f. using a laser to apply writings, graphics and/or other markings to the ampoules or vials, based upon product specifications/information/approved label as defined by the testing, the customer specifications, and regulatory governance.

11. The method of claim 10, wherein the applying comprises the step of removing laser light-blocking vapor, if present, by applying a short burst of dry air prior to applying the laser light to the previously affixed blank label.

12. The method of claim 1, wherein the applying is carried out in a temperature-controlled enclosure containing dry nitrogen gas, which gas is held at temperatures below about −70° C. or below about −80° C.

13. The method of claim 9, wherein the applying is carried out in a temperature-controlled enclosure containing dry nitrogen gas, which gas is held at temperatures below about −70° C. or below about −80° C.

14. The method of claim 1, further comprising the step of placing the marked vials into one or more cryogenic shipping vessel.

15. The method of claim 2, wherein the material in the vial is a vaccine.

16. The method of claim 15, wherein the vaccine is a cell-associated live vaccine.

17. The method of claim 15, wherein the vaccine loses less than about 0.2 log of titer during the labeling procedure.

18. The method of claim 17, wherein the vaccine loses less than about 0.1 log of titer during the labeling procedure.

19. The method of claim 3, wherein the material in the vial is a vaccine.

20. The method of claim 4, wherein the material in the vial is a vaccine.

21. The method of claim 5, wherein the material in the vial is a vaccine.

22. The method of claim 6, wherein the material in the vial is a vaccine.

23. The method of claim 7, wherein the material in the vial is a vaccine.

24. The method of claim 8, wherein the material in the vial is a vaccine.

25. The method of claim 9, wherein the material in the vial is a vaccine.

26. The method of claim 10, wherein the material in the vial is a vaccine.

27. The method of claim 11, wherein the material in the vial is a vaccine.

28. The method of claim 12, wherein the material in the vial is a vaccine.

29. The method of claim 13, wherein the material in the vial is a vaccine.

30. The method of claim 14, wherein the material in the vial is a vaccine.

* * * * *